United States Patent [19]

Breikss et al.

[11] Patent Number: 5,693,843
[45] Date of Patent: Dec. 2, 1997

[54] PROCESS FOR HYDROCYANATION OF DIOLEFINS AND ISOMERIZATION OF NONCONJUGATED 2 ALKYL-3-MONOALKENENITRILES

[75] Inventors: Anne Irisa Breikss, Hockessin; Thomas Foo, Wilmington, both of Del.

[73] Assignee: E. L Du Pont de Nemours and Company, Wilmington, Del.

[21] Appl. No.: 577,355

[22] Filed: Dec. 22, 1995

[51] Int. Cl.$^6$ .................... C07C 253/10; C07C 255/07
[52] U.S. Cl. .................... 558/338; 558/355; 558/356
[58] Field of Search .................... 558/338, 355, 558/356

[56] References Cited

U.S. PATENT DOCUMENTS

| 3,496,215 | 2/1970 | Drinkard et al. | 558/338 |
| 3,536,748 | 10/1970 | Drinkard et al. | 558/355 |
| 5,523,453 | 6/1996 | Breikss | 558/338 |

*Primary Examiner*—José G. Dees
*Assistant Examiner*—Laura L. Stockton

[57] ABSTRACT

Described herein is a process for the hydrocyanation of diolefins by employing a catalyst comprising the combination of a zero-valent nickel compound and certain bidentate phosphorus compounds, and a process for isomerizing 2-alkyl-3-monoalkenenitrile to form linear nitriles by the use of such catalyst.

9 Claims, No Drawings

PROCESS FOR HYDROCYANATION OF DIOLEFINS AND ISOMERIZATION OF NONCONJUGATED 2 ALKYL-3-MONOALKENENITRILES

FIELD OF THE INVENTION

This invention generally relates to an improved liquid phase process useful in the hydrocyanation of diolefinic compounds to produce nonconjugated acyclic olefin nitriles and to the subsequent liquid phase process of isomerization of said nitriles to 3-and/or 4-monoalkene linear nitriles. The improvement resides in conducting the process in the presence of zero-valent nickel and a bidentate phosphorus compound.

BACKGROUND OF THE INVENTION

Catalytic hydrocyanation systems, particularly pertaining to the hydrocyanation of olefins, are known in the art. For example, liquid phase systems useful for the hydrocyanation of butadiene to form pentenenitriles (PN) are known in the art. For example, Drinkard, U.S. Pat. No. 3,496,215, discloses the hydrocyanation of butadiene using monodentate nickel phosphite catalysts. As used in this patent, and as will be used herein, the term "pentenenitrile" is intended to mean cyanobutene. Likewise, "butenenitrile" means cyanopropene. Bidentate phosphite ligands complexed to zero-valent nickel and platinum are known to be useful in the liquid phase hydrocyanation of butadiene, as described by Baker et al. J. Chem. Soc., Chem. Commun., 1991, pages 803–804.

The pentenenitriles so formed are subjected to further hydrocyanation and/or isomerization to form adiponitrile (ADN), a commercially important material in the manufacture of nylon. For example, Drinkard, U.S. Pat. No. 3,536,748, discloses the liquid phase isomerization of 2-methyl-3-butenenitrile in the presence of a zero-valent nickel complex, and Chia, U.S. Pat. No. 3,676,481, discloses an improvement additionally utilizing tri(hydrocarbyl)boron promoters.

The hydrocyanation of activated olefins such as conjugated olefins (e.g., styrene) and strained olefins (e.g., norbornene) proceeds without the use of a Lewis Acid Promoter. For example, Casalnuovo, U.S. Pat. No. 5,175,335, discloses the use of chiral, nonracemic, bidentate phosphinite ligands for the enantioselective hydrocyanation of aromatic vinyl compounds. In contrast, the hydrocyanation of unactivated olefins such as 1-octene and 3-pentenenitrile normally requires the use of a Lewis Acid Promoter. Teachings regarding the use of a promoter in the hydrocyanation reaction appear, for example, in U.S. Pat. No. 3,496,217.

Bidentate phosphinite ligands used in the present invention for the hydrocyanation of diolefins have been used for the hydrocyanation of monoolefins. Commonly assigned, copending application Ser. No. U.S. Ser No. 08/408,250, filed Mar. 22, 1995 now U.S. Pat. No. 5,523,453 disclose such bidentate phosphinite ligands used in combination with a Lewis Acid Promoter to hydrocyanate monoolefins.

The present invention provides for an improved process for the hydrocyanation of diolefinic compounds, such as butadiene, and subsequent isomerization of monoolefins without the need for Lewis Acid Promoters utilizing zero-valent nickel and a bidentate phosphinite ligand. Other objects and advantages of the present invention will become apparent to those skilled in the art upon reference to the detailed description of the invention which hereinafter follows.

SUMMARY OF THE INVENTION

The present invention provides an improved process for the liquid phase hydrocyanation of diolefinic compounds and subsequent isomerization of the resulting nonconjugated acyclic nitriles comprising, reacting an aliphatic diolefinic compound, preferably butadiene, with a source of HCN, wherein the improvement comprises conducting the hydrocyanation and subsequent isomerization in the presence of a catalyst composition comprising zero-valent nickel and at least one bidentate phosphorus ligand selected from the group consisting of compounds represented by Formulas I through XIII:

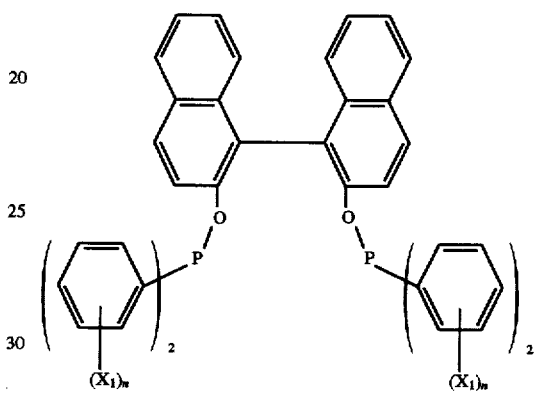

Formula I

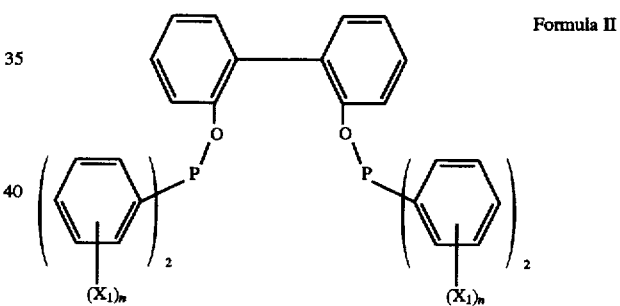

Formula II

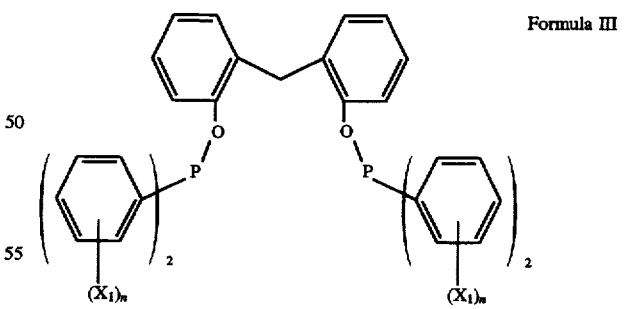

Formula III

-continued
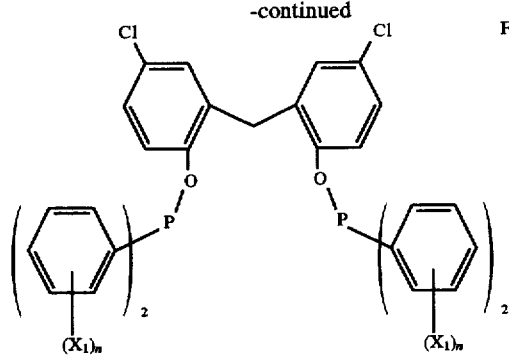
Formula IV
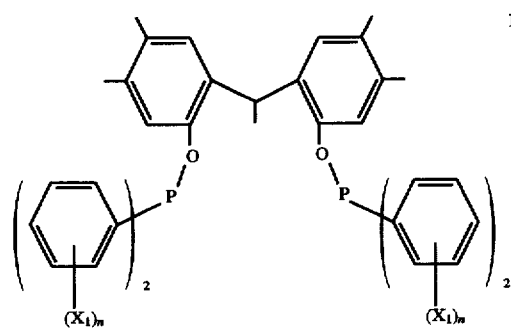
Formula V
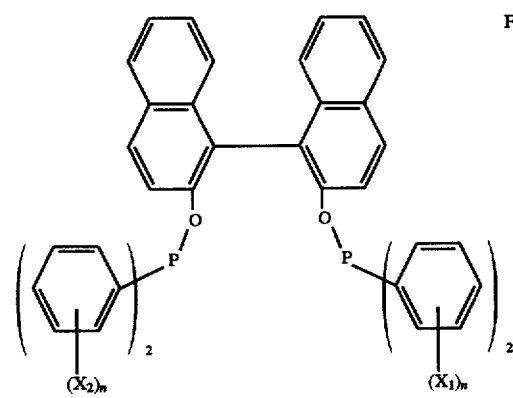
Formula VI
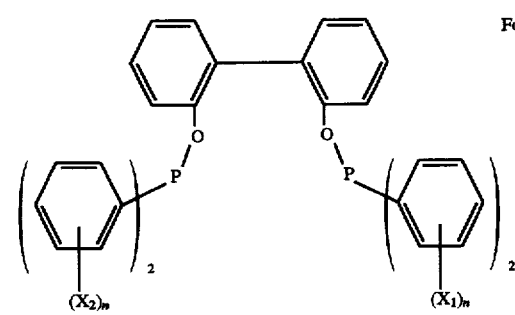
Formula VII
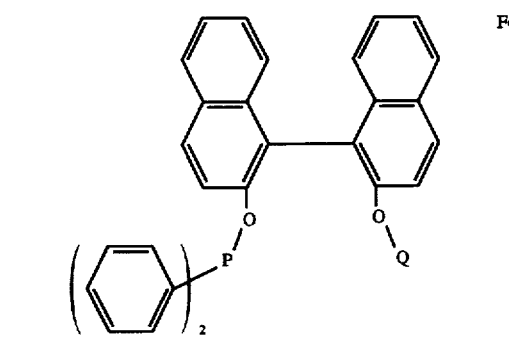
Formula VIII
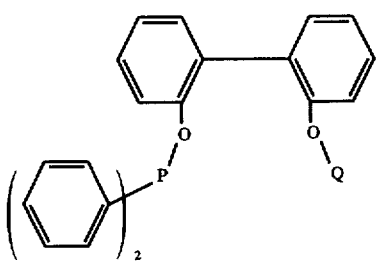
Formula IX
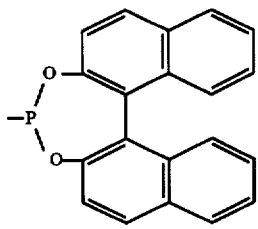
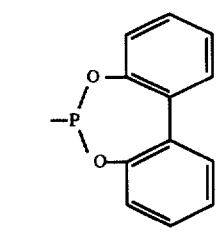
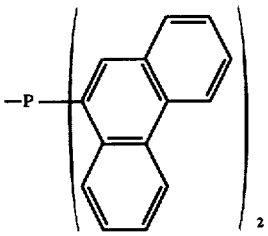
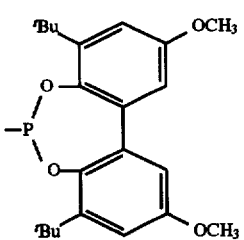
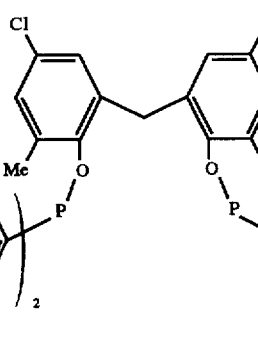
Formula X

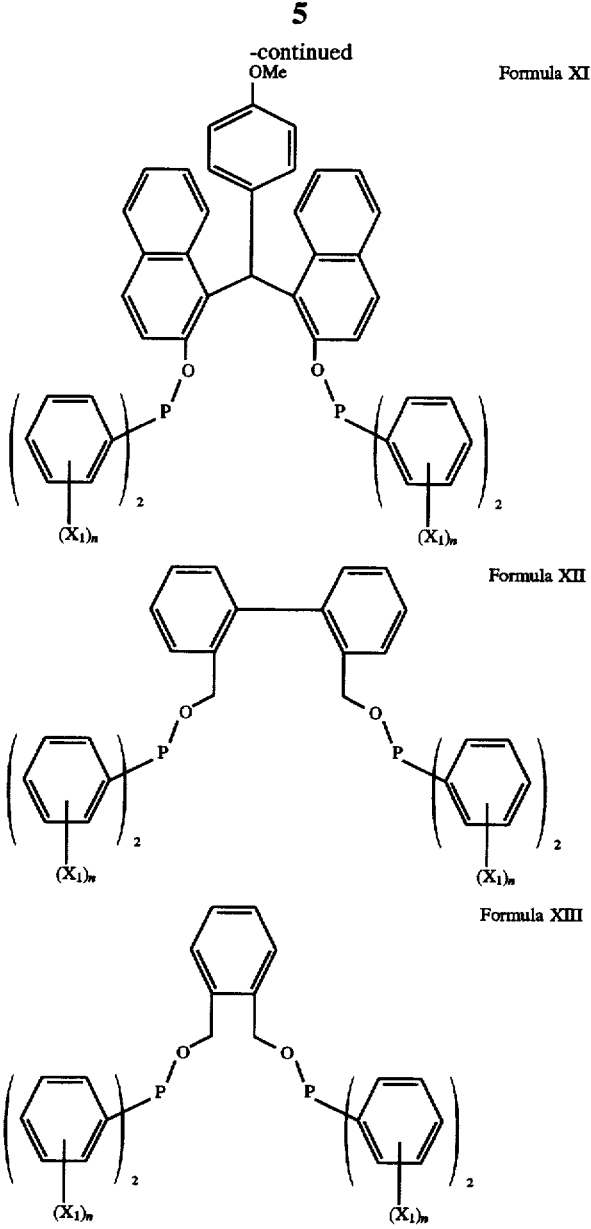

where $X_1$ is meta —Cl, para —Cl, meta —CF$_3$, para —CF$_3$, meta —F, para —F, meta —CN, para —CN, meta —CH$_3$, or para —CH$_3$; $X_2$ is methyl or alkoxy having 1 to 3 carbon atoms; n is zero, 1, or 2.

The reaction is most conveniently performed continuously from hydrocyanation of the starting diolefin to the final 3- and/or 4-monoalkene linear nitriles. However, the process can be conducted stepwise, i.e., the nonconjugated nitriles resulting from the hydrocyanation can be isolated per se, prior to isomerization. Furthermore, nonconjugated acyclic olefin nitriles prepared by any method can be used as starting materials for the isomerization in accordance with this invention.

DETAILED DESCRIPTION OF THE INVENTION

The catalyst precursor compositions useful for the practice of this invention are comprised of a bidentate phosphorus compound and zero-valent nickel. The catalyst composition is referred to as a "precursor" only to indicate, in all likelihood during the hydrocyanation reaction, the structure of the active catalyst composition may, in fact, be complexed to an olefin.

The bidentate phosphorus compounds may be prepared by a variety of methods known in the art. The symmetrical diphosphinites are prepared as follows. The diarylchlorophosphine is added to a toluene solution of a diol and triethylamine. The reaction mixture is allowed to stir at room temperature, then filtered to remove triethylamine hydrochloride. The product is isolated by removing the solvent under reduced pressure.

The unsymmetrical diphosphinites are prepared in a similar manner. The first diarylchlorophosphine (preferably the more sterically hindered one) is added to a toluene solution of a diol and triethylamine. Once the reaction is complete, the second diarylchlorophosphine is added. Triethylamine hydrochloride is filtered off and the solvent removed under reduced pressure to give the product.

The zero-valent nickel can be prepared or generated according to techniques known in the art (U.S. Pat. Nos. 3,496,217; 3,631,191; 3,846,461; 3,847,959; and 3,903,120, which are incorporated by reference). Zero-valent nickel compounds that contain ligands, which can be displaced by the organophosphorus ligand, are a preferred source of zero-valent nickel. Two such preferred zero-valent nickel compounds are Ni(COD)$_2$ (COD is 1,5-cyclooctadiene) and Ni(P(O-o-C$_6$H$_4$CH$_3$)$_3$)$_2$(C$_2$H$_4$), both of which are known in the art. Alternatively, divalent nickel compounds may be combined with a reducing agent and are then able to serve as suitable sources of zero-valent nickel in the reaction. Suitable divalent nickel compounds include compounds of the formula NiY$_2$ where Y is halide, carboxylate, or acetylacetonate. Suitable reducing agents include metal borohydrides, metal aluminum hydrides, metal alkyls, Zn, Fe, Al, Na, or H$_2$. Elemental nickel, preferably nickel powder, when combined with a halogenated catalyst, as described in U.S. Pat. No. 3,903,120, is also a suitable source of zero-valent nickel.

The actual catalyst is a complex of zero-valent nickel with the bidentate ligand, which is formed when those two materials are combined. An effective catalyst requires at least two moles of P atoms for one gram-atom of zero-valent nickel.

The diolefinic compound reactants used in this invention include primarily conjugated diolefins containing from 4 to 10 carbon atoms; for example, 1,3-butadiene, and cis- and trans-2,4-hexadienes, but also includes cis- and trans-1,3-pentadienes and 1,5-cyclooctadiene. Butadiene is especially preferred by reason of its commercial importance in the production of adiponitrile. Other suitable diolefinic compounds include diolefinic compounds substituted with groups which do not deactivate the catalyst.

The following Formulas XIV and XV illustrate suitable representative starting diolefinic compounds; and Formulas XVI, XVII, and XVIII represent the products obtained from 1,3-butadiene and HCN;

CH$_2$=CH—CH=CH$_2$     R$^1$—CH=CH—CH=CH—R$^2$

XIV                                    XV (1,3-butadiene)

wherein each one of R$^1$ and R$^2$, independently, is H or a C$_1$ to C$_3$ alkyl.

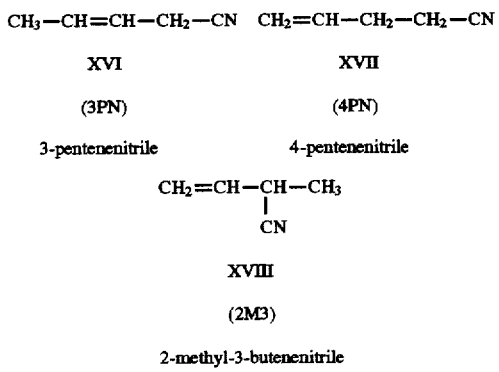

(3PN) 3-pentenenitrile (4PN) 4-pentenenitrile (2M3) 2-methyl-3-butenenitrile

It will be recognized that compound XIV 1,3-butadiene is a special case of Formula XV, where each one of $R^1$ and $R^2$ is hydrogen.

In the practice of the hydrocyanation of the diolefin in accordance with the present invention, the following description applies.

The hydrocyanation reaction can be carried out with or without a solvent. Any solvent should be a liquid at the reaction temperature and inert towards the unsaturated compound and the catalyst. Generally, such solvents are hydrocarbons such as benzene, xylene, or nitriles such as acetonitrile, benzonitrile, or adiponitrile.

The exact temperature used is dependent, to a certain extent, on the particular catalyst being used, the particular unsaturated compound being used and the desired rate. Generally, temperatures of from −25° C. to 200° C. can be used with from 0° C. to 150° C., being the preferred range.

The reaction may be carried out by charging a reactor with all of the reactants, or preferably, the reactor is charged with the catalyst or catalyst components, the unsaturated compound and any solvent used, and the hydrogen cyanide gas is swept over the surface of the reaction mixture or bubbled through said reaction mixture. If desired, when using a gaseous unsaturated organic compound, the hydrogen cyanide and the unsaturated organic compound may be fed together into the reaction medium. The molar ratio of unsaturated compound to catalyst generally is varied from about 10:1 to 100,000:1, preferably 100:1 to 5,000:1, unsaturated compound to catalyst for a batch operation. In a continuous operation, such as when using a fixed bed-catalyst type of operation, a higher proportion of catalyst may be used such as 5:1 to 100,000:1, preferably 100:1 to 5,000:1, unsaturated compound to catalyst.

Preferably, the reaction mixture is agitated, such as by stirring or shaking.

The cyanated product can be recovered by conventional techniques such as crystallization of the product from solution or by distillation.

One can either isolate the 2-alkyl-3-monoalkenenitriles produced by the hydrocyanation of the diolefin or proceed continuously with the isomerization under similar reaction conditions.

The 2-alkyl-3-monoalkenenitrile used as the starting materials in the isomerization of this invention can result from the hydrocyanation of diolefin described above or can come from any other available source. The olefinic double bond in the 2-alkyl-3-monoalkenenitrile used as the starting materials in the isomerization of this invention cannot be conjugated to the triple bond of the cyano group. Suitable starting 2-alkyl-3-monoalkenenitriles can also carry groups which do not attack the catalyst, for example, another cyano group. Preferably, the starting 2-alkyl-3-monoalkenenitriles contain from 5 to 8 carbon atoms, excluding any additional substitution. 2-methyl-3-butenenitrile is especially important in the production of adiponitrile. Other representative nitriles include 2-ethyl-3-butenenitrile and 2-propyl-3-butenenitrile.

The following Formulas XIX and XX illustrate suitable representative starting 2-alkyl-3-monoalkenenitriles. When the starting nitrile is 2-methyl-3-butenenitrile, the isomerization products are those shown in Formulas XXI and XXII:

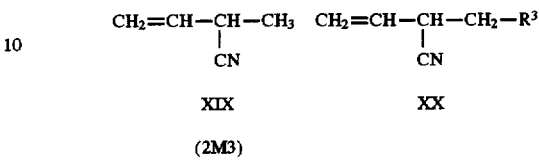

(2M3)

wherein $R^3$ is H or a $C_1$ to $C_3$ alkyl.

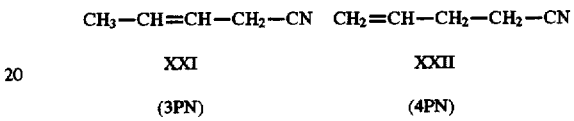

(3PN)  (4PN)

It will be recognized that Formula XIX is a special case of Formula XX, where $R^3$ is hydrogen.

The isomerization process of this invention can be carried out, for example, at atmospheric pressure and at any temperature in the range of 10°–200° C., preferably in the range of 60°–150° C. The pressure is not critical, however, and can be above or below atmospheric pressure, if desired. Any of the conventional batch or continuous flow procedures may be used either in the liquid phase or in the vapor phase (with respect to the relatively volatile 2-methyl-3-butenenitrile reactant and linear pentenenitrile products). The reactor may be of any mechanically and chemically resistant material and is usually of glass or an inert metal or alloy, e.g., nickel, copper, silver, gold, platinum, stainless steel, Monel®, Hastelloy®, etc.

The process is usually carried out "neat," i.e., without an added diluent or solvent. Any solvent or diluent that is nondestructive of the catalyst can be used, however. Suitable solvents include aliphatic or aromatic hydrocarbons (hexane, cyclohexane, benzene), ethers (diethyl ether, tetrahydrofuran, dioxane, glycol dimethyl ether, anisole), esters (ethyl acetate, methyl benzoate), nitriles (acetonitrile, benzonitrile), etc.

A nonoxidizing environment is desirable in order to retard oxidative deactivation of the catalyst. Accordingly, an inert atmosphere, e.g., nitrogen, is normally and preferably used, although air may be used, if desired, at the expense of loss of a proportion of the catalyst through oxidation.

When the process is a typical batch operation in the liquid phase with or without a solvent, the catalytic nickel complex is soluble to some extent at temperatures within the operating range and is usually completely soluble at the most preferred operating temperature. However, the nickel complex is essentially nonvolatile, whereas the 2-methyl-3-butenenitrile reactant, and the linear pentenenitrile products are relatively volatile. Accordingly, in a continuous flow procedure, the catalyst may be a component of the flowing system in a completely liquid-phase operation, it may be in a mobile nonflowing liquid state in a semi-vapor-phase operation, or it may be in a fixed-bed state (usually on a solid support) in a conventional flowing vapor-phase operation.

The time element in the process is not critical and may generally be governed by practical considerations. The time required for a practical level of conversion of 2-methyl-3-butenenitrile to linear pentenenitriles is dependent upon the temperature of the reaction, i.e., operation at lower temperature generally requires a longer time than operation at a higher temperature. A practical reaction time can be in the range of a few seconds to many hours, depending on the particular conditions and method of operation.

The molar ratio of 2-methyl-3-butenenitrile to catalyst is generally greater than 1:1, usually in the range from about 5:1 to 20,000:1, preferably 100:1 to 5,000:1, for a batch or continuous operation.

In a preferred process, the bidentate phosphorus compound is of Formula I, where each X is $CF_3$, Cl, or F and n=0, 1, or 2.

EXAMPLES

The invention will now be illustrated by the following non-limiting examples of certain preferred embodiments thereof, wherein all parts, proportions, and percentages are by weight, unless otherwise indicated.

Example 1

A 25 wt % solution of 1,3-butadiene was made by vacuum transfer of 9.11 g of 1,3-butadiene into 27.33 g of butyronitrile. A 25 wt % solution of HCN was made by the addition of 2.506 g of HCN to 7.503 g of propionitrile. The catalyst solution was prepared by the addition of 0.055 g of $Ni(COD)_2$ and 0.474 g of the ligand having the structure labeled "Example 1" below to 9.47 g of propionitrile. With these solutions, the following reaction mixtures were prepared in 2-ml GC vials equipped with micro-stirbars:

|  | Sample 1 | Sample 2 | Sample 3 |
|---|---|---|---|
| Butadiene Solution | 0.206 g | 0.202 g | 0.205 g |
| HCN Solution | 0.080 g | 0.081 g | 0.085 g |
| Catalyst Solution | 0.080 g | 0.077 g | 0.077 g |

The GC vials were crimp-sealed with caps fitted with appropriately sized sheets of Nordel rubber to aid in containing the reaction mixtures. The vials were placed in a hot-block-stirrer set at 80° C. Sample 1 was removed after 1.0 h of reaction time. Sample 2 was removed after 2.0 h of reaction time. Sample 3 was removed after 3.0 h of reaction time. The reaction was quenched in each case by diluting the reaction mixture with diglyme as a GC solvent for product analysis. The propionitrile in the reaction mixture was used as an internal standard in the GC product analysis. The results of the analyses are shown in Table 1.

TABLE 1

| BUTADIENE HYDROCYANATION | | | | |
|---|---|---|---|---|
| EXAMPLE | TIME | % 3PN | % 2M3 | TOTAL PN |
| 1 | 1 hr. | 34.9% | 70.8% | 105.6% |
|   | 2 hr. | 34.8% | 68.8% | 103.5% |
|   | 3 hr. | 35.6% | 70.9% | 106.4% |
| 2 | 1 hr. | 34.3% | 71.0% | 105.3% |
|   | 2 hr. | 34.9% | 68.4% | 103.3% |
|   | 3 hr. | 35.6% | 65.4% | 101.0% |
| 3 | 1 hr. | 33.4% | 66.8% | 100.2% |
|   | 2 hr. | 32.3% | 64.2% | 96.5% |
|   | 3 hr. | 31.2% | 62.8% | 94.0% |
| 4 | 1 hr. | 36.1% | 64.3% | 100.4% |
|   | 2 hr. | 31.9% | 59.1% | 91.0% |
|   | 3 hr. | 31.0% | 61.7% | 92.7% |
| 5 | 1 hr. | 34.0% | 57.3% | 91.3% |
|   | 2 hr. | 33.5% | 56.9% | 90.4% |
|   | 3 hr. | 34.0% | 57.1% | 91.1% |
| 6 | 1 hr. | 18.4% | 55.1% | 73.5% |
|   | 2 hr. | 21.3% | 63.0% | 84.3% |
|   | 3 hr. | 21.9% | 65.0% | 87.0% |
| 7 | 1 hr. | 26.3% | 69.3% | 95.6% |
|   | 2 hr. | 27.3% | 68.2% | 95.5% |

TABLE 1-continued

| BUTADIENE HYDROCYANATION | | | | |
|---|---|---|---|---|
| EXAMPLE | TIME | % 3PN | % 2M3 | TOTAL PN |
|   | 3 hr. | 21.7% | 59.6% | 81.3% |
| 8 | 30 | 33.4% | 69.7% | 103.0% |
|   | 1 hr. | 32.0% | 62.9% | 94.9% |
|   | 2 hr. | 28.8% | 51.9% | 80.7% |
| 9 | 1 hr. | 7.6% | 49.9% | 57.5% |
|   | 2 hr. | 9.6% | 52.9% | 62.5% |
|   | 3 hr. | 10.3% | 55.0% | 65.3% |
| 10 | 1 hr. | 6.0% | 14.0% | 20.0% |
|   | 2 hr. | 10.6% | 24.2% | 34.8% |
|   | 3 hr. | 14.0% | 31.8% | 45.8% |
| 11 | 1 hr. | 2.5% | 8.8% | 11.2% |
|   | 2 hr. | 8.0% | 20.1% | 28.1% |
|   | 3 hr. | 12.9% | 30.2% | 43.1% |
| 12 | 1 hr. | 7.9% | 25.8% | 33.7% |
|   | 2 hr. | 8.8% | 27.9% | 36.7% |
|   | 3 hr. | 8.4% | 27.3% | 35.7% |
| 13 | 1 hr. | 11.7% | 21.8% | 33.5% |
|   | 2 hr. | 11.1% | 20.7% | 31.9% |
|   | 3 hr. | 11.8% | 22.0% | 33.7% |
| 14 | 1 hr. | 8.3% | 23.7% | 32.0% |
|   | 2 hr. | 9.2% | 23.4% | 32.6% |
|   | 3 hr. | 9.4% | 22.4% | 31.8% |
| 15 | 1 hr. | 8.0% | 24.9% | 32.9% |
|   | 3 hr. | 7.7% | 24.2% | 31.9% |
|   | 4 hr. | 7.4% | 23.5% | 30.9% |

In the examples as shown in Table 1, the butadiene hydrocyanation experiments were performed as follows.

Example 2 through 15 were run in a manner similar to Example 1, except that the solvent for the components might have differed. All solvents for these examples were chosen from propionitrile, butyronitrile, or hexanenitrile.

In the examples as shown in Table 2, the 2M3 isomerization experiments were performed as follows. A sample containing 81 to 83% of 2-methyl-3-butenenitrile (2M3), with other pentenenitrile isomers, was the starting material.

Example 16

The catalyst solution was prepared by the addition of 0.055 of $Ni(COD)_2$ and 0.439 g of the ligand having the structure labeled "Example 16" below to 9.51 g of propionitrile. A sample of 2M3BN was distilled under nitrogen onto 100 parts per million of 2,6-di-tert-butyl-4-methylphenol. GC analysis of this sample showed it to be 81% 2M3BN. With these mixtures, the following reaction mixtures were prepared in 2-ml GC vials equipped with micro-stirbars:

|  | Sample 0 | Sample 1 | Sample 2 |
|---|---|---|---|
| Catalyst Solution | 0.085 g | 0.112 g | 0.101 g |
| 2M3BN | 0.084 g | 0.111 g | 0.101 g |

The GC vials were crimp-sealed with caps fitted with appropriately sized sheets of Nordel rubber to aid in containing the reaction mixtures. Samples 1–2 were placed in a hot-block-stirrer set at 125° C. Sample 0 represented the t=0. Sample 1 was removed after 1.0 h of reaction time. Sample 2 was removed after 2.0 h of reaction time. The reaction was quenched in each case by diluting the reaction mixture with diglyme as a GC solvent for product analysis. The propionitrile in the reaction mixture was used as an internal standard in the GC product analysis. The results of the analyses are shown in Table 2.

TABLE 2

2-METHYL-3-BUTENENITRILE ISOMERIZATION

| EXAMPLE | TIME | % 2M3 | % 3PN |
|---|---|---|---|
| 16 | 0 hr. | 106.5% | 1.7% |
|  | 1 hr. | 41.7% | 66.6% |
|  | 2 hr. | 38.0% | 71.5% |
| 17 | 0 hr. | 101.2% | 1.9% |
|  | 1 hr. | 44.5% | 59.4% |
|  | 2 hr. | 43.6% | 68.5% |
|  | 3 hr. |  | 70.0% |
| 18 | 0 hr. | 98.6% | 1.4% |
|  | 1 hr. | 43.9% | 50.8% |
|  | 2 hr. | 39.9% | 55.4% |
|  | 3 hr. | 41.5% | 56.2% |
| 19 | 0 hr. | 89.5% | 1.0% |
|  | 1 hr. | 64.3% | 34.7% |
|  | 2 hr. | 68.2% | 37.6% |
|  | 3 hr. | 56.4% | 33.8% |
| 20 | 0 hr. | 100.1% | 1.2% |
|  | 1 hr. | 85.0% | 13.1% |
|  | 2 hr. | 76.9% | 16.6% |
|  | 3 hr. | 63.1% | 30.7% |

Examples 17–20 were run in a manner similar to Example 16 using the ligands designated below.

The structures of bidentate phosphorous compounds used in the examples are shown below:

Structures for Examples in Table 1

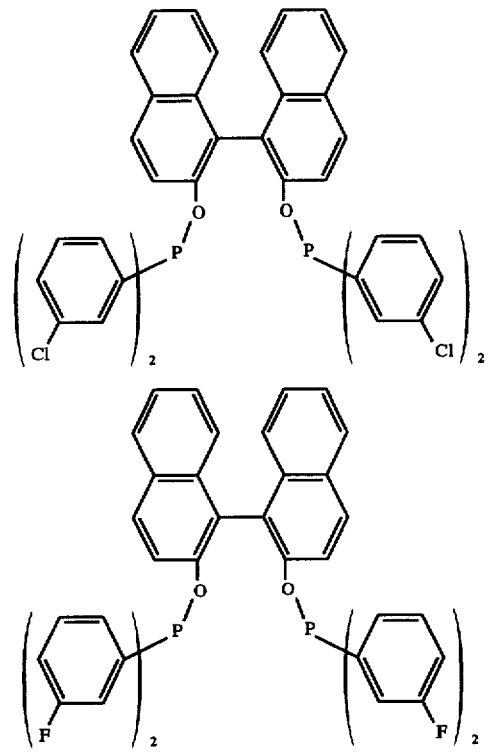

Example 1

Example 2

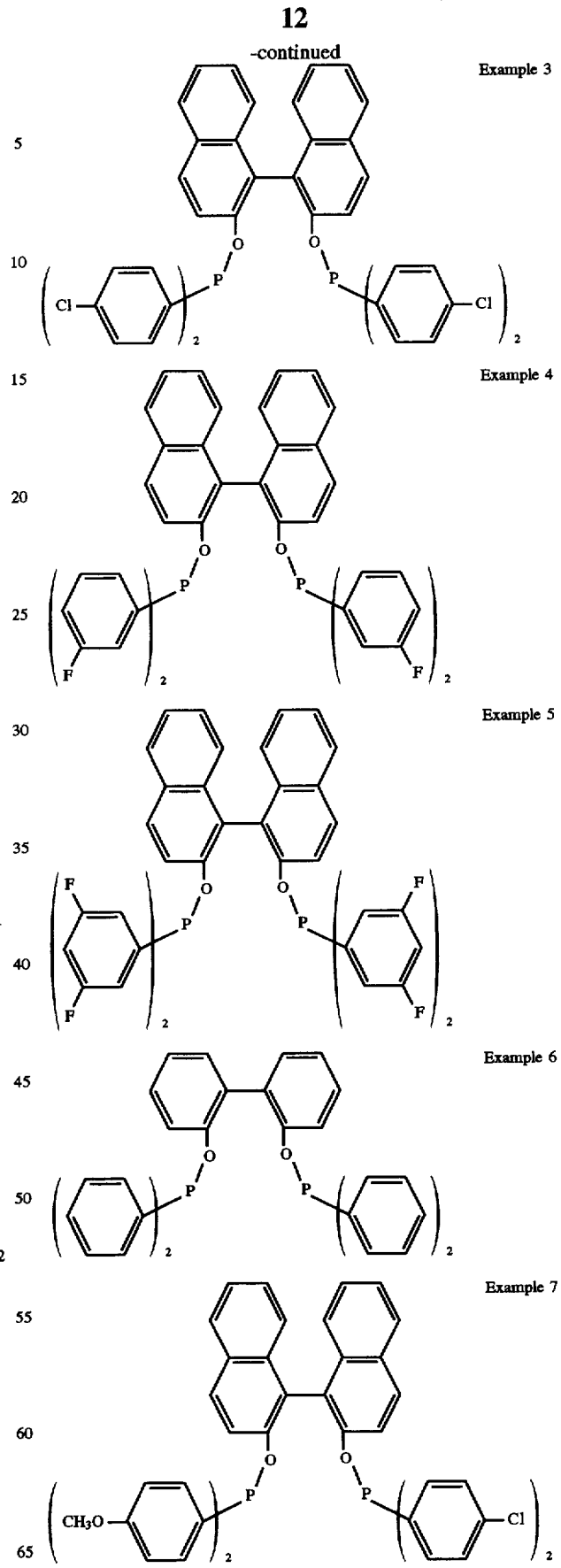

-continued

Example 3

Example 4

Example 5

Example 6

Example 7

Example 8
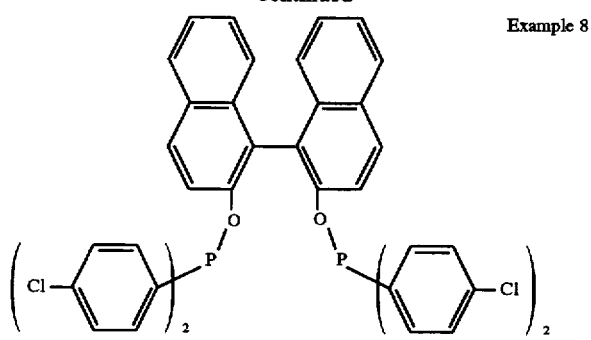
Example 9
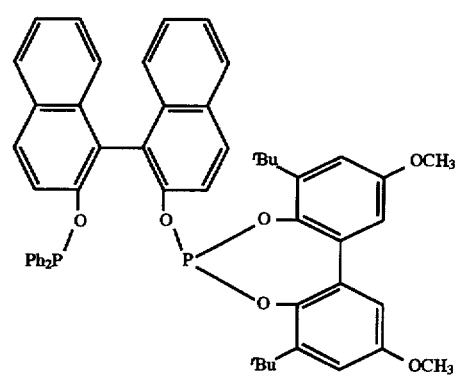
Example 10
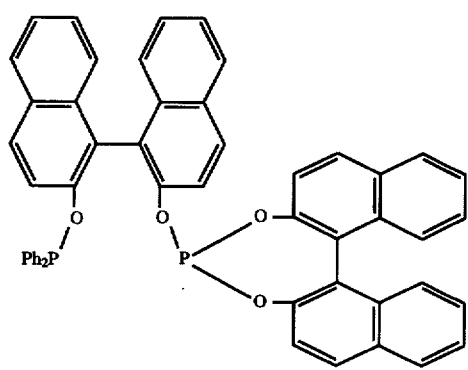
Example 11
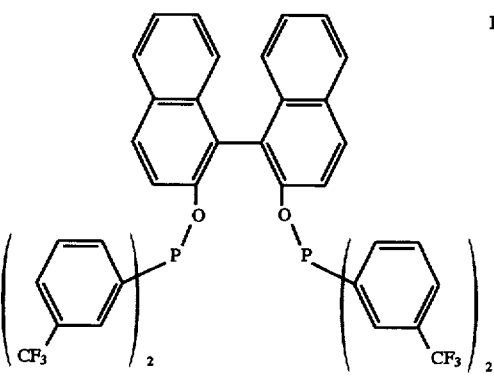
Example 12
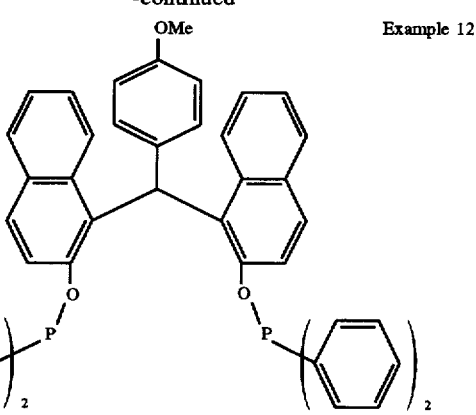
Example 13
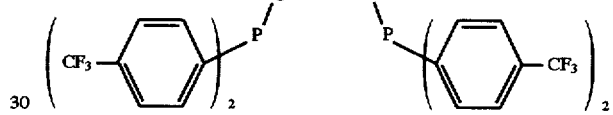
Example 14
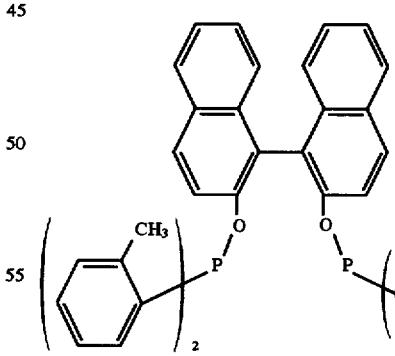
Example 15

Structures for Examples in Table 2

Example 16

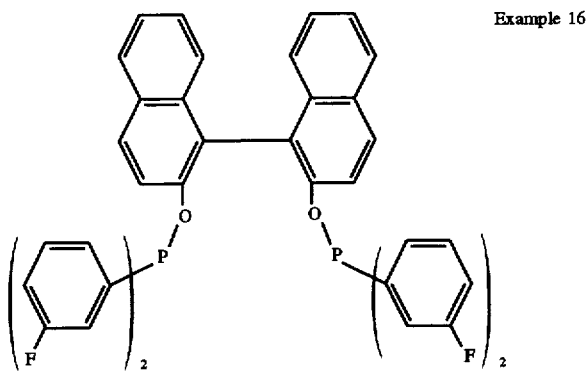

Example 17

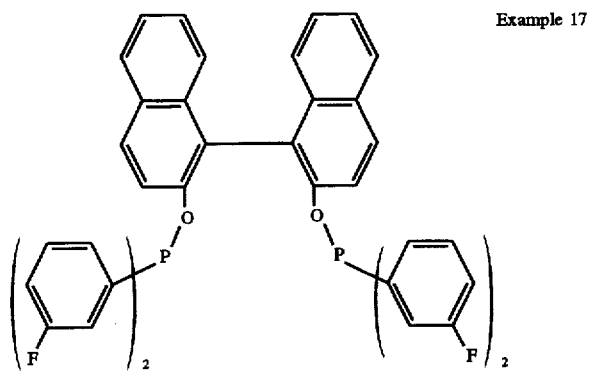

Example 18

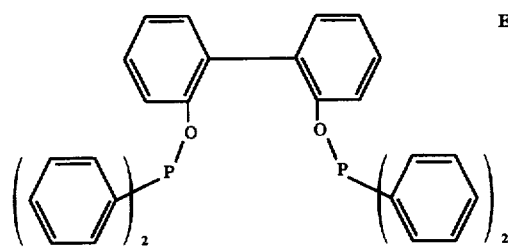

Example 19

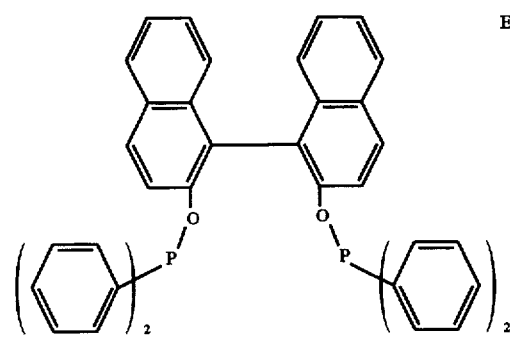

Example 20

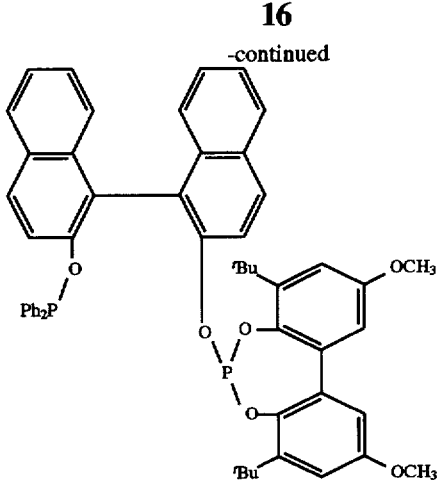

What is claimed is:

1. A process for the liquid phase hydrocyanation of an aliphatic diolefin having 4 to 10 carbon atoms which comprises reacting said diolefin with HCN at a temperature in the range of −25° to 200° C. in the presence of a catalyst comprising a zero-valent nickel compound and at least one bidentate phosphorus compound selected from the group consisting of compounds of the formula Formula I

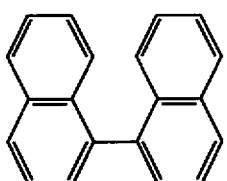

Formula II

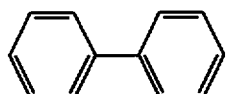
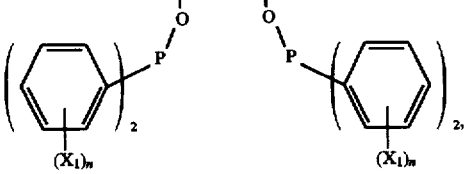

Formula III

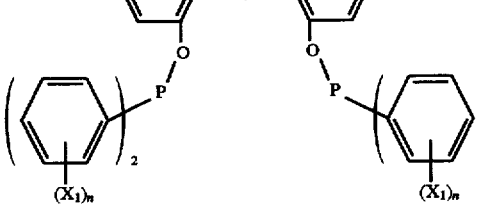

-continued
Formula IV
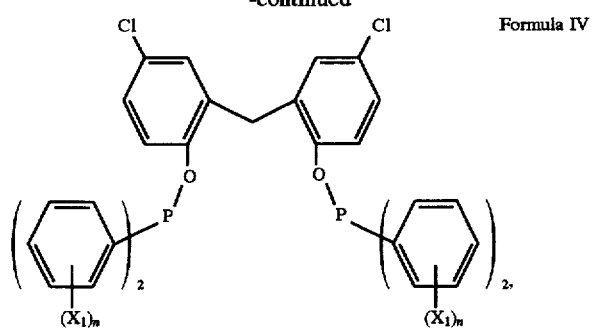
Formula V
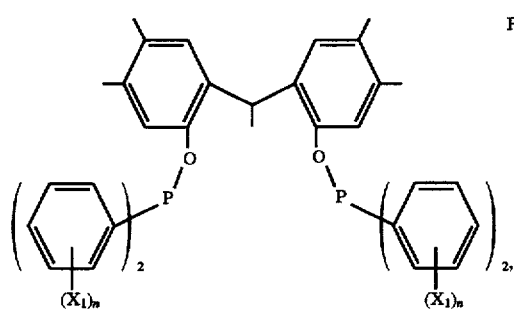
Formula VI
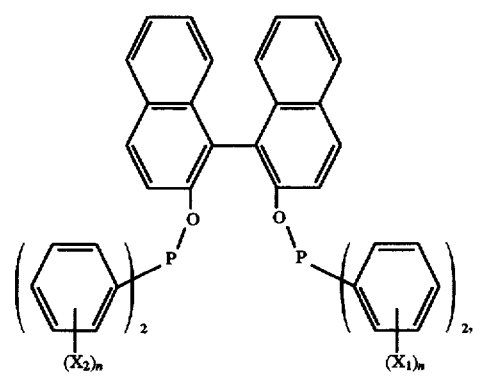
Formula VII
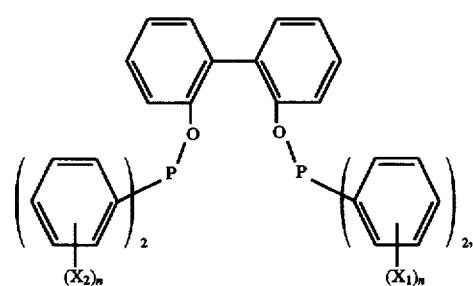
Formula VIII
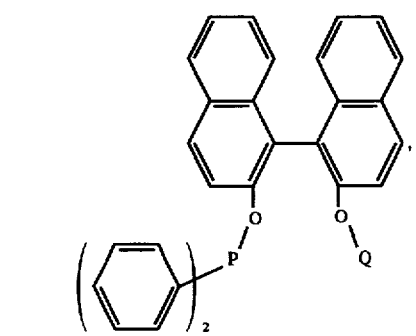
Formula IX
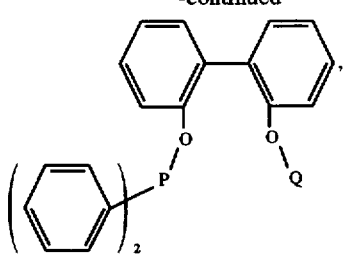
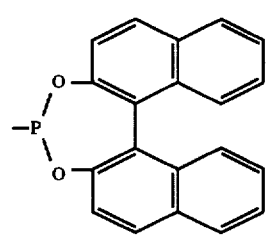
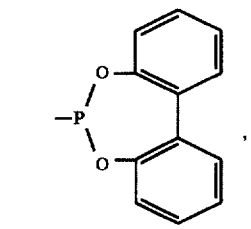
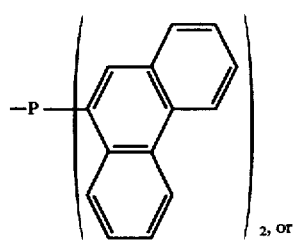
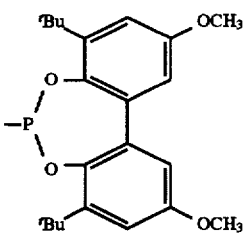
Formula X
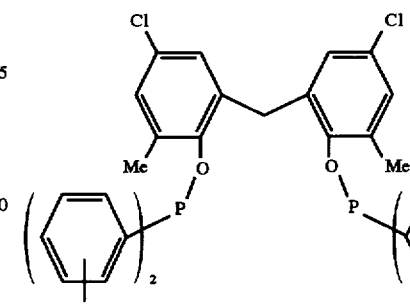

pounds of the formula

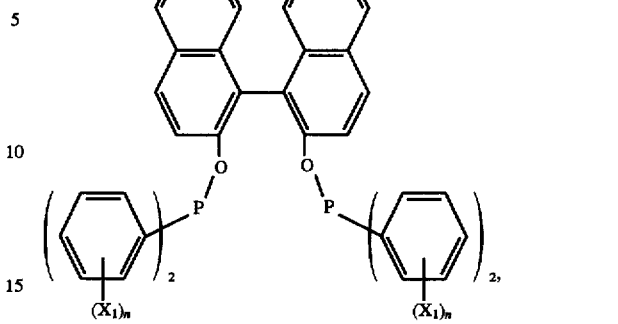

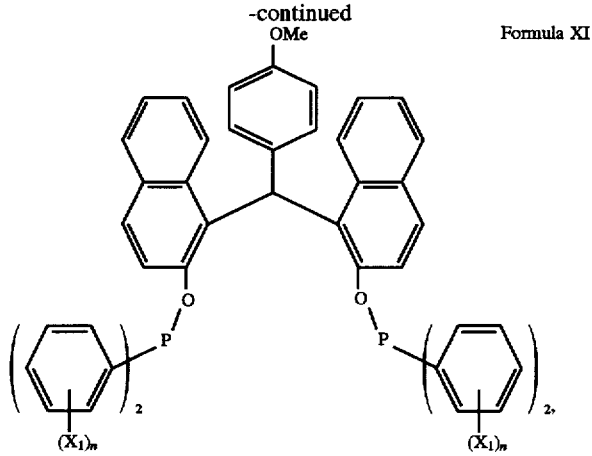

where $X_1$ is meta —Cl, para —Cl, meta —CF$_3$, para —CF$_3$, meta —F, para —F, meta —CN, para —CN, meta —CH$_3$ or para —CH$_3$; $X_2$ is methyl or alkoxy having 1 to 3 carbon atoms; n is zero, 1, or 2.

2. The process of claim 1 in which the diolefin is selected from the group consisting of 1,3-butadiene, cis and trans-2,4-hexadienes, cis and trans-1,3-pentadienes, and 1,5-cyclooctadiene.

3. The process of claim 1 in which the diolefin is a conjugated acyclic aliphatic diolefin containing 4 to 10 carbon atoms.

4. The process of claim 1 in which the molar ratio of the aliphatic diolefin to catalyst is between 100:1 and 5000:1.

5. The process of claim 1 in which the bidentate phosphorus compound is selected from Formula I and Formula II.

6. The process of claim 5 in which the bidentate phosphorus compound is from Formula I and each $X_1$ is CF$_3$, Cl, or F and n=0, 1, or 2.

7. A process for the liquid phase hydrocyanation of an aliphatic diolefin having 4 to 10 carbon atoms to form a mixture containing nonconjugated acylic nitriles comprising 2-alkyl-3-monoalkenenitrile which comprises reacting said diolefin with HCN at a temperature in the range of −25° to 200° C. in the presence of a catalyst comprising a zerovalent nickel compound and at least one bidentate phosphorus compound selected from the group consisting of com-

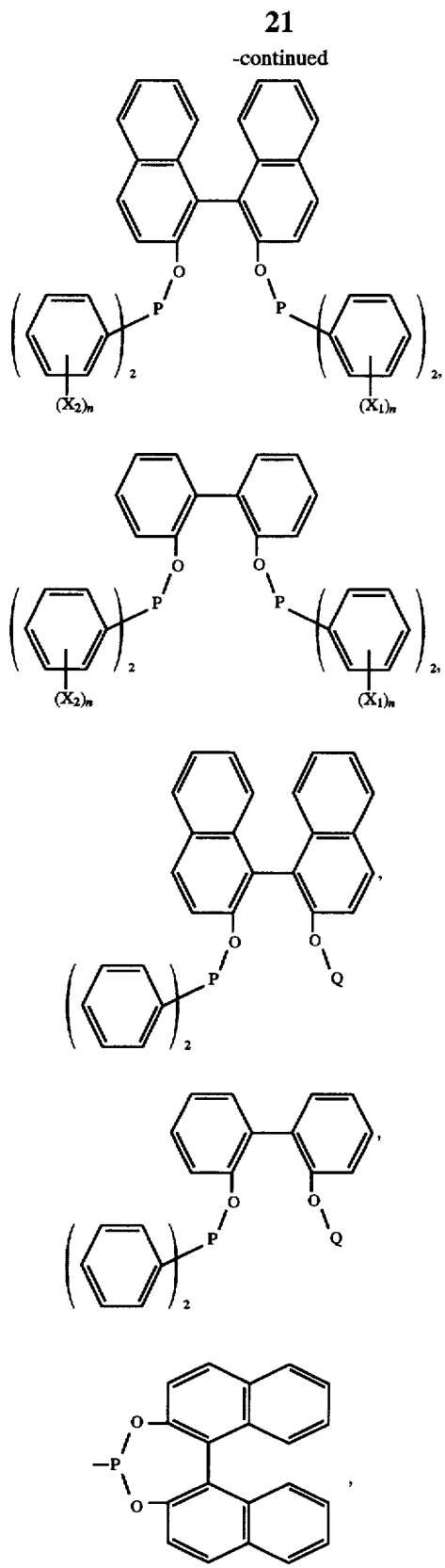
Formula VI
Formula VII
Formula VIII
Formula IX
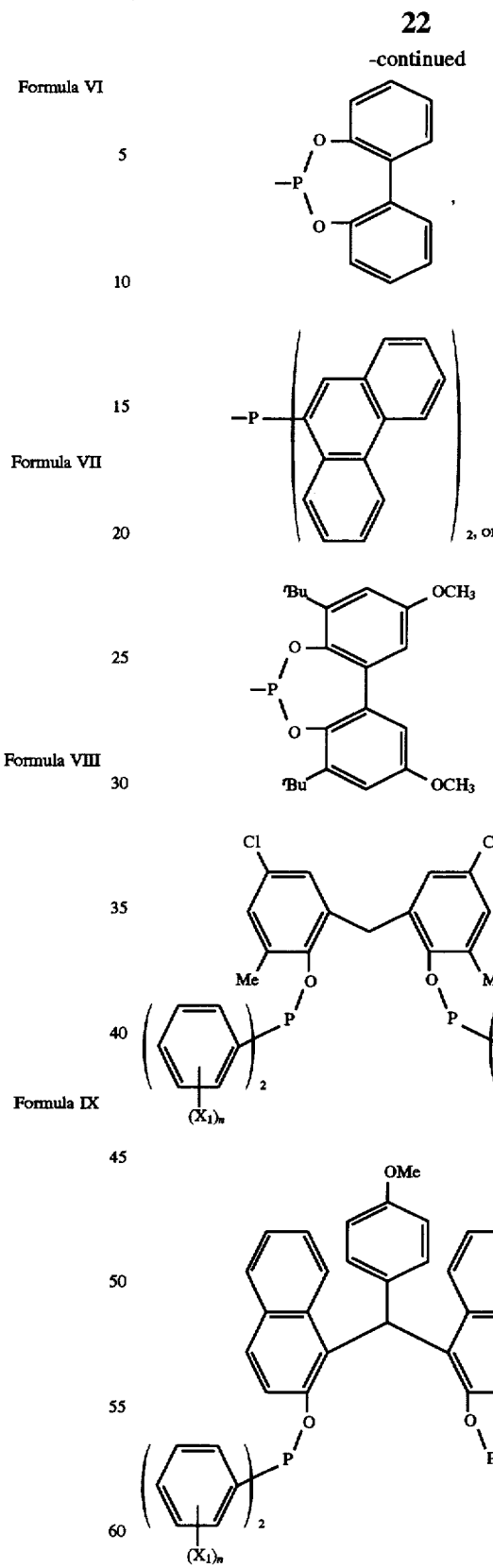
Formula X
Formula XI -continued Formula XII

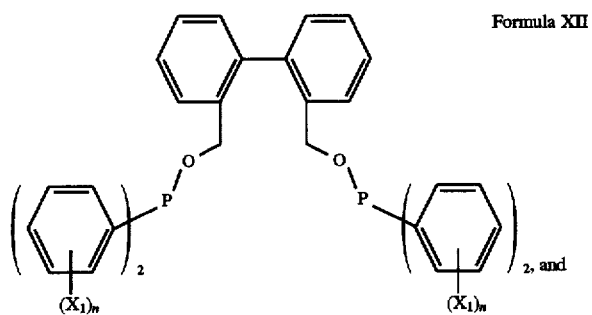

Formula XIII

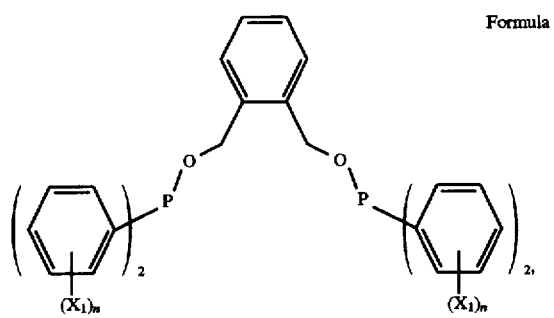

where $X_1$ is meta —Cl, para —Cl, meta —CF$_3$, para —CF$_3$, meta —F, para —F, meta —CN, para —CN, meta —CH$_3$, or para —CH$_3$; $X_2$ is methyl or alkoxy having 1 to 3 carbon atoms; n is zero, 1, or 2, and then isomerizing the 2-alkyl-3-monoalkenenitrile contained in the mixture to form 3- and/or 4-monoalkene linear nitriles by reacting said mixture in the presence of the catalyst comprising the nickel compound and the at least one bidentate phosphorus compound at a temperature in the range of 10° to 200° C.

8. A process for isomerizing 2-alkyl-3-monoalkenenitrile contained in a mixture of nonconjugated nitriles to form 3- and/or 4- monoalkene linear nitriles which comprises contacting said mixture with a catalyst comprising a zero-valant nickel compound and at least one bidentate phosphorus compound selected from the group consisting of compounds of the formula Formula I

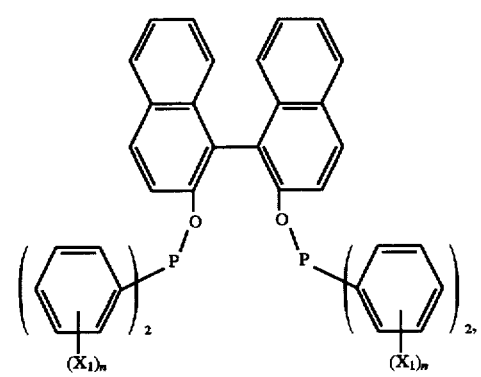

-continued

Formula II

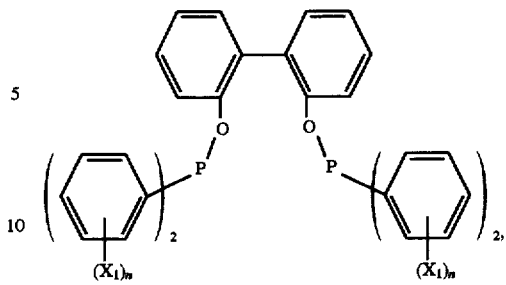

Formula III

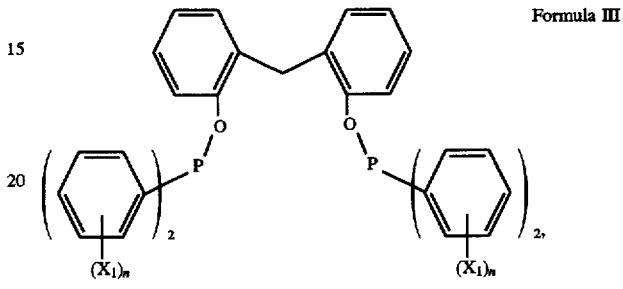

Formula IV

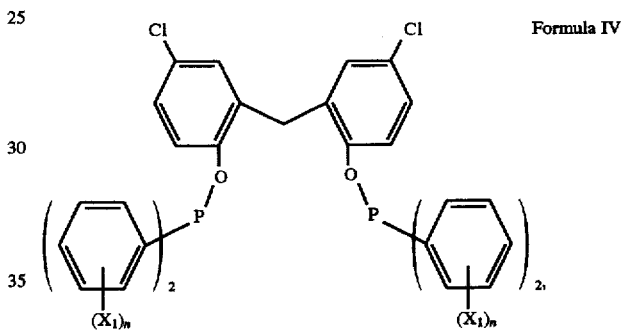

Formula V

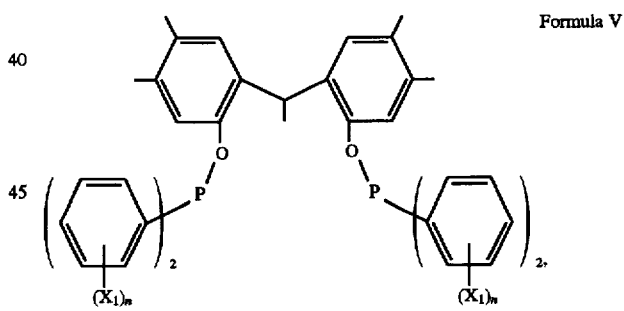

Formula VI

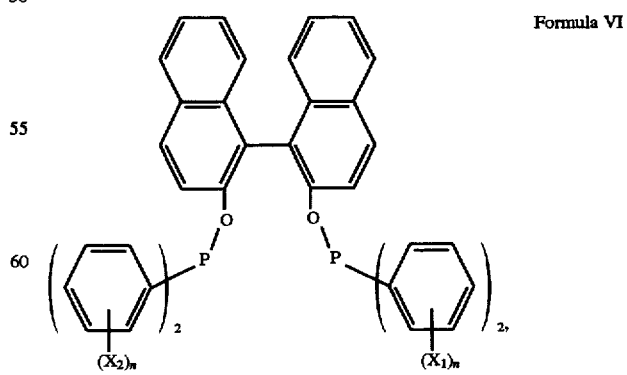

Formula VII
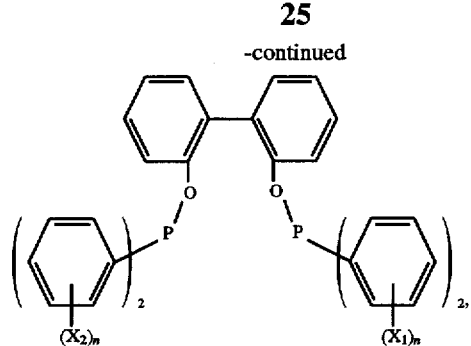
Formula VIII
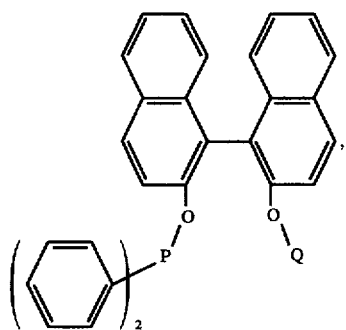
Formula IX
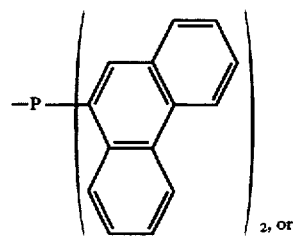
Formula X
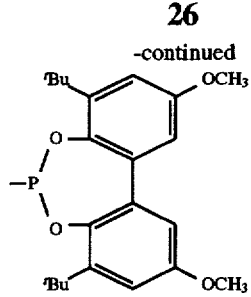
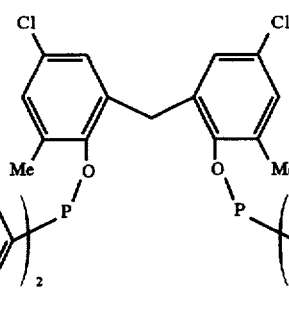
Formula XI
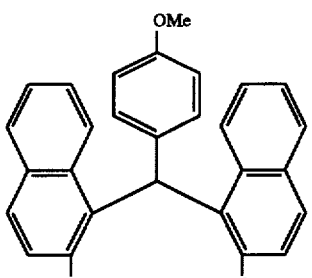
Formula XII
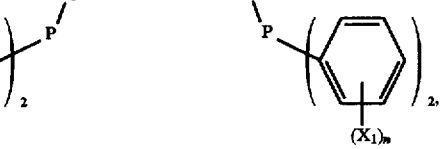
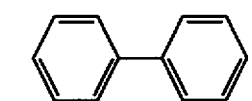, and
Formula XIII
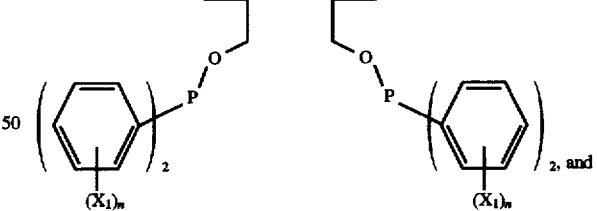

where $X_1$ is meta —Cl, para —Cl, meta —CF$_3$, para —CF$_3$, meta —F, para —F, meta —CN, para —CN, meta —CH$_3$, or para —CH$_3$; $X_2$ is methyl or alkoxy having 1 to 3 carbon atoms; n is zero, 1 or 2.

9. The process of claim 1 in which the aliphatic diolefin is butadiene.